United States Patent [19]

Yoshida et al.

[11] Patent Number: 4,990,433
[45] Date of Patent: Feb. 5, 1991

[54] METAL-CONTAINING INDOANILINE COMPOUND AND OPTICAL RECORDING MEDIUM EMPLOYING THE COMPOUND

[75] Inventors: Katsuhira Yoshida; Yuji Kubo, both of Kochi, Japan

[73] Assignee: Mitsubishi Kasei Corporation, Tokyo, Japan

[21] Appl. No.: 378,041

[22] Filed: Jul. 11, 1989

Related U.S. Application Data

[62] Division of Ser. No. 100,264, Sep. 23, 1987, Pat. No. 4,873,332.

[30] Foreign Application Priority Data

Mar. 14, 1987 [JP] Japan .................................. 62-59777

[51] Int. Cl.$^5$ .................................................. G03C 1/00
[52] U.S. Cl. ..................................... 430/495; 430/270; 430/945; 428/64
[58] Field of Search ....................... 430/495, 270, 945; 428/64

[56] References Cited

U.S. PATENT DOCUMENTS 4,737,443  4/1988  Niwa et al. ........................... 430/270

OTHER PUBLICATIONS

Kubo et al., Chemistry Letters 1563–1566 (8/87).

"Program and Abstracts II" of the 53rd Autumn Conference, pub. Sep. 26, 1986.

*Primary Examiner*—Paul R. Michl
*Assistant Examiner*—Ashley I. Pezzner
*Attorney, Agent, or Firm*—Oblon, Spivak, McClelland, Maier & Neustadt

[57] ABSTRACT

An optical recording medium of a metal-containing indoaniline compound having the formula:

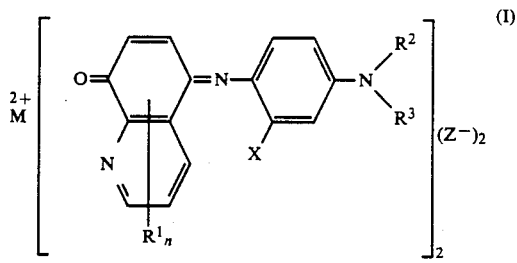

wherein M is a metal atom selected from the group consisting of Ni, Cu or Co, $R^1$ is a hydrogen atom, a halogen atom or a methyl group, n is 1 or 2, X is a hydrogen atom or a lower alkyl group, each of $R^2$ and $R^3$ is a lower alkyl group, and $Z^-$ is an anion, as a dye on a substrate.

10 Claims, 4 Drawing Sheets

METAL-CONTAINING INDOANILINE COMPOUND AND OPTICAL RECORDING MEDIUM EMPLOYING THE COMPOUND

This is a division of application Ser. No. 07/100,264, filed on Sept. 23, 1987, now U.S. Pat. No. 4,873,332.

BACKGROUND OF THE INVENTION

1. Field of the Invention

The present invention relates to a metal-containing indoaniline compound useful for optical recording which utilizes the laser technology and an optical recording medium employing the compound.

2. Discussion of Background

In recent years, the optical recording utilizing laser has been developed particularly for the storage of high density information recording and reproduction of the recorded information.

An optical disc may be mentioned as a typical example of such optical recording medium.

In general, the optical disc is designed for high density information recording which is effected by irradiation of a laser beam collimated to have a diameter of about 1 μm onto a thin recording layer formed on a substrate of a disc shape. The information recording is effected by a thermal deformation of the recording layer, such as the decomposition, evaporation or dissolution, which takes place upon absorption of the laser beam energy at the irradiated portions of the recording layer. On the other hand, the reproduction of the recorded information is done by reading a difference in the reflectance between the portion thermally deformed by the laser beam and the portion where no such deformation has occurred.

Accordingly, the optical recording medium is required to have high absorptivity for a laser beam of a particular wavelength used for the recording since it is required to absorb the energy of the laser beam efficiently, and also to have a high reflectance to the laser beam of a particular wavelength for use in the reproduction so as to carry out the accurate reproduction of the recorded information.

Various constructions have been proposed for the optical recording medium of this type.

For example, Japanese Unexamined Patent Publication No. 97033/1980 discloses a medium having a single layer of a phthalocyanine dye formed on a substrate. However, the phthalocyanine dye is poor in the sensitivity and has a difficulty such that its decomposition temperature is high and its vapor deposition is difficult. Besides, its solibility in an organic solvent is extremely poor, and it is hardly possible to apply it by coating.

Japanese Unexamined Patent Publication No. 83344/1983 discloses a recording medium having a recording layer composed of a phenalene dye, and Japanese Unexamined Patent Publication No. 224793/1983 discloses a recording medium having a recording layer composed of a naphthoquinone dye. However, such a dye has a drawback that the reflectivity is low while it has an advantage that it can readily be vapor-deposited. If the reflectivity is low, the contrast in the reflectance between the non recorded portion and the recorded portion irradiated with the laser beam tends to be low, and the reproduction of the recorded information tends to be difficult. Further, in general, an organic dye has a drawback that it is inferior in the storage stability.

SUMMARY OF THE INVENTION

It is an object of the present invention to provide a metal-containing indoaniline compound which is highly soluble in an organic solvent and thus capable of being applied by coating and which has a high reflectivity and thus is useful for optical recording with a good contrast and excellent storage stability.

Another object of the present invention is to provide an optical recording medium employing such a compound.

The present invention provides a metal-containing indoaniline compound having the formula:

wherein M is a metal atom selected from the group consisting of Ni, Cu or Co, $R^1$ is a hydrogen atom, a halogen atom or a methyl group, n is 1 or 2, X is a hydrogen atom or a lower alkyl group, each of $R^2$ and $R^3$ is a lower alkyl group, and $Z^-$ is an anion.

The present invention provides also an optical recording medium comprising a substrate and a recording layer containing a dye formed on the substrate wherein the recording is effected by irradiation of a laser beam to occur a thermal deformation of the recording layer and the reproduction is done by reading a difference in the reflectance between the deformed portion and the undeformed portion, said dye being a metal-containing indoaniline compound of the formula I.

DETAILED DESCRIPTION OF THE PREFERRED EMBODIMENTS

Now, the structure of the metal-containing indoaniline compound of the formula I will be described in detail.

In the formula I, the anion represented by $Z^-$ may be, for example, $I^-$, $Br^-$, $Cl^-$ or $ClO_4^-$. Particularly preferred is $ClO_4^-$.

The lower alkyl group represented by X may be an alkyl group having from 1 to 4 carbon atoms such as a methyl group, an ethyl group, a propyl group or a butyl group. An alkyl group having 1 or 2 carbon atoms is preferred. Particularly preferred is an ethyl group. Such an alkyl group may be of a straight chain or branched.

A lower alkyl group represented by each of $R^2$ and $R^3$ may be an alkyl group having from 1 to 7 carbon atoms such as a methyl group, an ethyl group, a propyl group, a butyl group, a pentyl group or a hexyl group. An alkyl group having from 2 to 4 carbon atoms is preferred. Such an alkyl group may be of a straight chain or branched.

$R^1$ is a hydrogen atom, a halogen atom or a methyl group, preferably a hydrogen atom.

n is 1 or 2. When n is 2, the two $R^1$ may be the same or different groups.

M is a metal atom selected from the group consisting of Ni, Cu and Co, preferably Ni or Co.

Among the metal-containing indoaniline compounds of the present invention, particularly preferred are those represented by the formula:

wherein each of $R^4$ and $R^5$ is an alkyl group having from 2 to 4 carbon atoms.

The metal-containing indoaniline compound of the formula I has an absorption in the wavelength range of from 600 to 800 nm, and a molecular absorption coefficient of from $10^4$ to $10^5$ cm$^{-1}$.

The synthesis of the metal-containing indoaniline compound of the formula I of the present invention may usually be conducted, for example, as disclosed in the collection of preliminary reports for the 53rd Autumn manual meeting of Japan Chemical Association, 1986, 639 by Yuji Kubo, Kyoko Sasaki and Katsuhira Yoshida. Namely, the compound of the formula I may be prepared by subjecting the compound of the formula:

wherein $R^1$ and n are as defined above, to oxidative condensation with a hydrochloride of a compound of the formula:

wherein X, $R^2$ and $R^3$ are as defined above, to obtain a compound of the formula:

wherein $R^1$, $R^2$, $R^3$, X and n are as defined above, and then reacting the compound of the formula IV with a metal salt of the formula:

wherein M and $Z^-$ are as defined above.

The metal-containing indoaniline compound of the present invention may be used as a dye for the optical recording medium. The optical recording medium is composed basically of a substrate and a recording layer containing the metal-containing indoaniline compound. If necessary, an underlayer may be formed on the substrate, or a protective layer may be formed on the recording layer.

The substrate may be transparent or opaque to the laser beam to be used. The substrate may be made of a material commonly used for a support for recording materials, such as glass, plastic, paper or a metal in a sheet or foil form. However, the plastic is most suitable from various viewpoints. The plastic includes an acrylic resin, a methacrylate resin, a vinyl acetate resin, a vinyl chloride resin, nitrocellulose, a polyethylene resin, a polypropylene resin, a polycarbonate resin, a polyimide resin, an epoxy resin and a polysulfone resin. Among them, a methacrylate resin and a polycarbonate resin are preferred.

When the metal-containing indoaniline compound of the present invention is used as an information recording layer in an optical recording medium, the thickness of the layer is usually from 100 Å to 5 μm, preferably from 1000 Å to 3 μm. The layer may be formed by employing a thin layer-forming method commonly empolyed, such as a vacuum vapor deposition method, a sputtering method, a doctor blade method, a casting method, a spinner method or a dipping method. If necessary, a binder may be employed. As such a binder, a conventional binder such as PVA, PVP, nitrocellulose, cellulose acetate, polyvinyl butyral or polycarbonate may be used. The weight ratio of the metal-containing indoaniline compound to the resin is preferably at least 0.01. When the layer is formed by a spinner method, the rotational speed is preferably from 500 to 5000 rpm. In some cases, after the spin coating, heat treatment or treatment with a solvent vapor may be applied.

Further, for the purpose of improving the stability or light-resistance of the recording medium, the recording layer may contain a transition metal chelate compound (such as acetyl acetonate chelate, bisphenol dithiol, salicylaldehyde oxime or bisdithio-α-diketone) as a Singlet oxygen quencher.

Further, an additional dye may be incorporated. The additional dye may be a different compound of the same type or a dye of different type such as a triaryl methane dye, an azo dyestuff, a cyanine dye or squalerium dye.

When the recording layer is formed by a doctor blade method, a casting method, a spinner method or a dipping method, particularly by a coating method such as a spinner method, a solvent having a boiling point of from 120° to 160° C. such as tetrachloroethane, bromoform, dibromoethane, ethyl cellosolve, xylene, chlorobenzene or cyclohexanone is suitably employed as the solvent for coating.

The recording layer of the optical recording medium may be provided on each side of the substrate, or on one side only.

Recording of information onto the recording medium thus obtained, is effected by irradiatinq a laser beam, preferably a semiconductor laser beam, collimated to have a diameter of about 1 μm onto the recording layer formed on each side or one side of the substrate. A thermal deformation such as the decomposition, evaporation or fusion due to the absorption of the laser energy takes place at the portions of the recording layer irradiated by the laser beam.

Reproduction of the recorded information is done by reading a difference in the reflectance between the portion where the thermal deformation occurred by the laser beam and the portion where no such thermal deformation took place.

The laser beam useful for the optical recording medium includes a $N_2$ laser, a He-Cd laser, an Ar laser, a He-Ne laser, a rubby laser, a semiconductor laser and a color laser. A semiconductor laser is particularly preferred from the viewpoint of the light weight, easiness in handling and compact structure.

Now, the present invention will be described in further detail with reference to Examples. However, it should be understood that the present invention is by no means restricted by such specific Examples.

EXAMPLE 1

(a) Preparation

886 mg of hydrochloride of 2-amino-5-diethylaminotoluene having the formula:

was dissolved in 150 ml of water, and 260 mg of sodium hydrogencarbonate and 250 mg of sodium hydroxide were added thereto and stirred. Then, 100 ml of an aqueous solution containing 300 mg of a compound having the formula:

and 166 mg of sodium hydroxide, was added thereto, and 6.2 ml of 5% sodium hypochlorite as dropwise added thereto at 5° C. Formed precipitates were separated by filtration and subjected to column chromatography separation (silica gel; developing solvent: ethyl acetate/benzene=1/1) to obtain 5-(2'-methyl-4'-diemthylaminophenylimino)quinoline-8-one having the formula:

(yield: 64.3%).

The melting point of this compound was from 125° to 128° C., and the visible range absorption spectrum (in chloroform) was $\lambda_{max}$ 626 nm ($\epsilon_{max}$ 18400). The results of the elemental analysis are as shown below, where the analytical values and the calculated values are in good agreement.

| | ($C_{20}H_{21}N_3O$) | | |
| --- | --- | --- | --- |
| | C | H | N |
| Calculated values (%) | 75.23 | 6.58 | 13.17 |
| Analytical values (%) | 76.03 | 6.69 | 13.06 |

Figure 1:
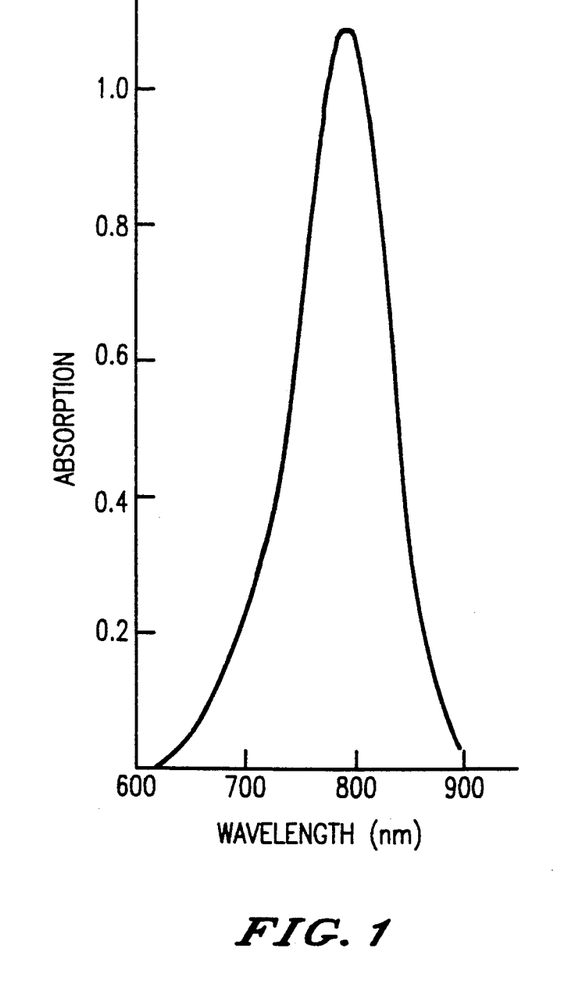
FIGS. 1, 3 and 4 show the visible range absorption spectra of three metal-containing indoaniline compounds of the present invention, respectively. In each Figure, the ordinate represents the absorbance and the abscissa represents the wavelength (nm).

Then, a solution prepared by dissolving 285.3 mg of $Ni(ClO_4)_2.6H_2O$ in 50 ml of water, was added under a nitrogen atmosphere to a solution prepared by dissolving 100 mg of 5-(2'-methyl-4'-diethylaminophenylimino)quinoline-8-one obtained above in 50 ml of 99% ethanol, and the mixture was stirred at room temperature for about 30 minutes. Formed precipitates were subjected to suction filtration, washed with water and dried to obtain a metal-containing indoaniline compound having the formula:

The melting point of this compound was from 245° to 246° C., and the visible range absorption spectrum (in chloroform) was $\lambda_{max}$ 795 nm (FIG. 1) ($\epsilon_{max}$ 122000).

(b) Recording medium-1

Figure 2:
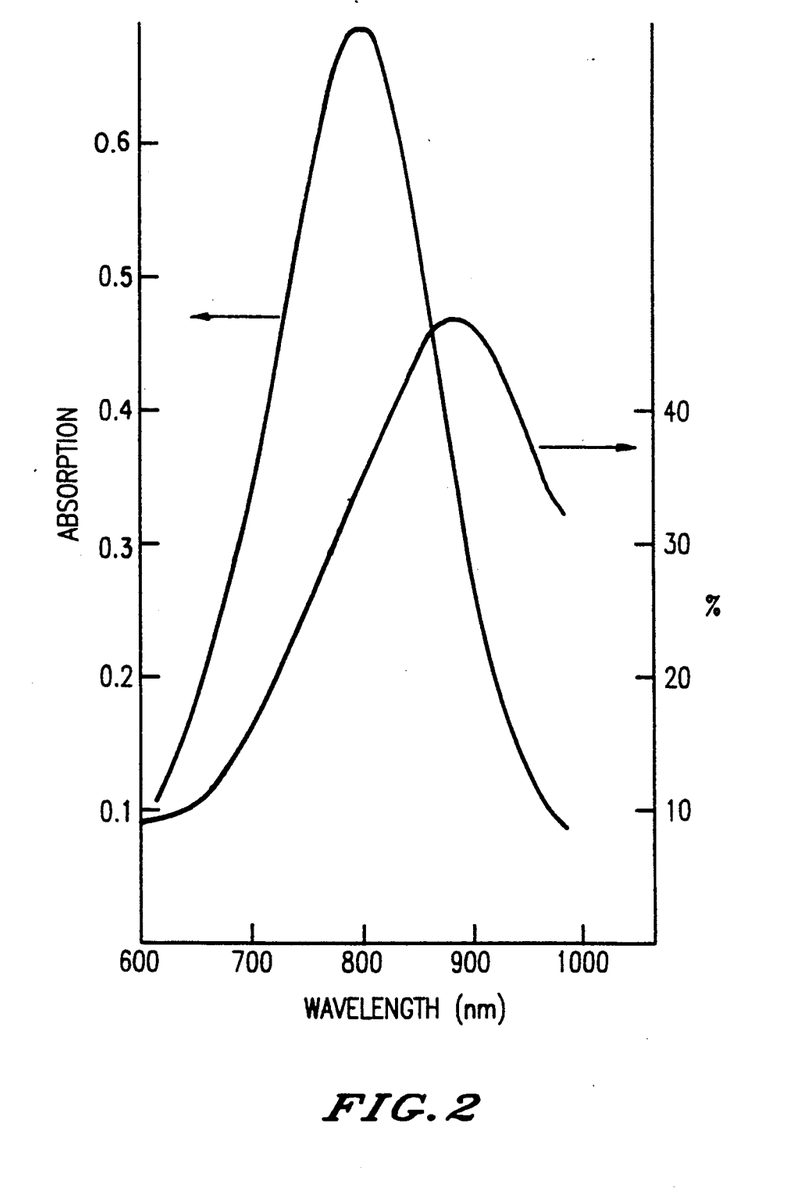
FIG. 2 shows the absorption spectrum and reflection spectrum of a thin coating layer of a metal-containing indoaniline compound of the present invention. The ordinate at the left represents the absorbance and the ordinate at the right represents the reflectance. The absissa represents the wavelength (nm).

0.1 g of the metal-containing indoaniline compound prepared in step (a) was dissolved in 10 g of tetrachloroethane, and filtered through a 0.22 μ filter to obtain a solution. Then, 1 ml of this solution was dropped onto a substrate (52 mm in diameter) of a polymethyl methacrylate (PMMA) resin, and coated by a spinner method at a rotational speed of 800 rpm. After the coating, the coating layer was dried at 60° C. for 10 minutes. The maximum absorption wavelength of the coating layer was 808 nm, and the reflectance was 38% (830 nm). The shape of the spectrum was broad. FIG. 2 shows the absorption and reflection spectra of the coating layer.

(c) Optical recording-1

To the coating layer obtained in step (b), a semiconductor laser beam having a central wavelength of nm was irradiated at an output of 4 mW, whereby pits having a very clear and distinct profile and having a pit depth of 790 Å (as measured by ELIONIX measurement) were Further, to this coating layer, a semiconductor laser beam having a central wavelength of 780 nm was irradiated at an output of 6 mW, whereby pits having a very clear and distinct profile and having a pit depth of 1155 Å (as measured by ELIONIX measurement) were formed.

This coating layer was stable for at least 20 days in an accelerated test under a high temperature and high humidity condition (60° C., 80% RH).

(d) Recording medium-2

0.1 g of the metal-containing indoaniline compound prepared in step (a) was dissolved in 10 g of tetrachloroethane, and filtered through a 0.22 μ filter to obtain a solution. Then, 5 ml of this solution was dropped onto a PMMA resin substrate (5 inch) having grooves with a depth of 700 Å and a width of 0.7 μm formed by an ultraviolet curable resin, and coated by a spinner method at a rotational speed of 900 rpm. After the coating layer was dried at 60° C. for 10 minutes.

(e) Optical recording-2

While rotating the 5 inch PMMA resin substrate having a layer of the above recording medium at a speed of 4 m/sec, a semiconductor laser beam having a central wavelength of 830 nm was irradiated thereto with a pulse width of 500 nsec, whereby the C/N ratio was 52 dB at an output of 6 mW. The storage stability (60° C., 80% RH) was good.

(f) Recording medium-3

0.1 g of the metal-containing indoaniline compound prepared in step (a) was dissolved in 10 g of ethyl cellosolve, and filtered through a 0.22 μ filter to obtain a solution. Then, 5 ml of this solution was dropped onto a polycarbonate resin substrate (injection molded product, 5 inch) having a thickness of 1.2 mm and provided with grooves with a pitch of 1.6 μm, and coated by a spinner method at a rotational speed of 800 rpm. After the coating, the coating layer was dried at 60° C. for 10 minutes.

(g) Optical recording-3

While rotating the 5 inch polycarbonate resin substrate having a layer of the above recording medium at a speed of 4 m/sec, a semiconductor laser beam having a central wavelength of 830 nm was irradiated thereto with a pulse width of 500 nsec, whereby the C/N ratio was 50 dB at an output of 6 mW. The storage stability (60° C., 80% RH) was good.

EXAMPLE 2

(a) Preparation

The operation was conducted in the same manner as in Example 1 except that 86.8 mg of the compound having the formula:

was used instead of 100 mg of the compound of the formula:

in Example 1, whereby a metal-containing indoaniline compound having the formula:

was obtained.

Figure 3:
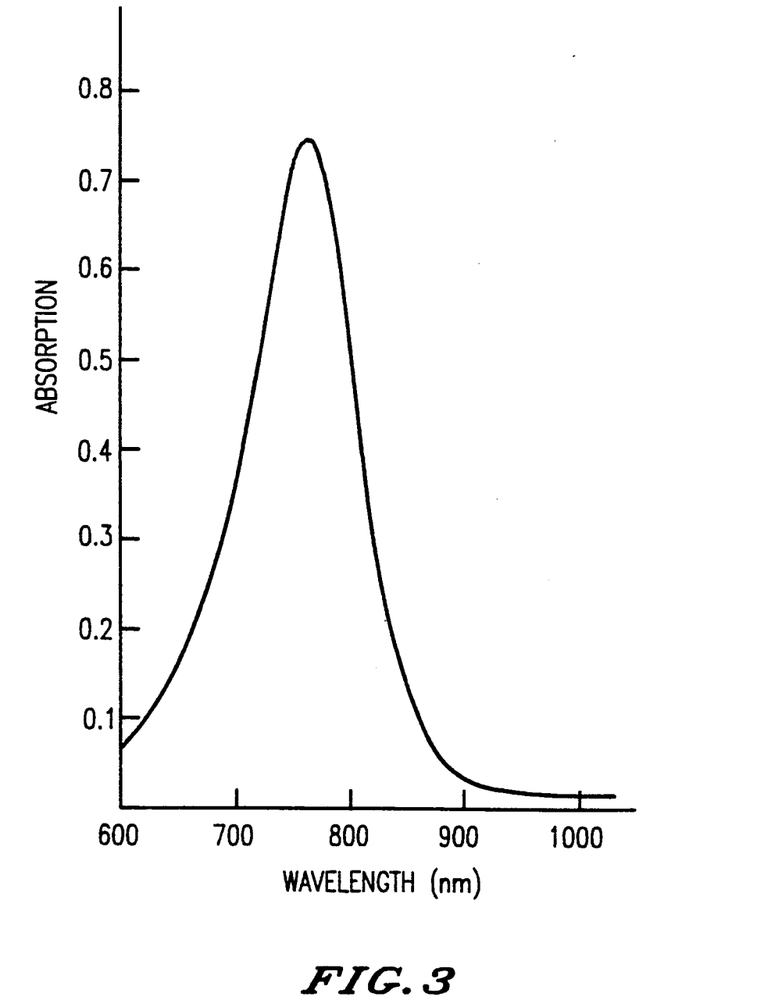

The melting point of this compound was over 300° C., and the visible range absorption spectrum (in chloroform) was $\lambda_{max}$ 766 nm (FIG. 3).

(b) Recording medium

In the same manner as in Example 1, the metal-containing indoaniline compound prepared in step (a) was coated by a spinner method onto a PMMA resin substrate provided with grooves. The maximum absorption wavelength of the coating layer was 778 nm, and the shape of spectrum was broad.

(c) Optical recording

While rotating the above PMMA resin substrate at a speed of 4 m/sec, a semiconductor laser beam having a central wavelength of 780 nm was irradiated thereto with a pulse width of 500 nsec, whereby the C/N ratio was 50 dB at an output of 6 mW. The storage stability (60° C., 80% RH) was good.

EXAMPLE 3

(a) Preparation

The operation was conducted in the same manner as in Example 1 except that 289 mg of $Cu(ClO_4)_2.6H_2O$ was used instead of 285.3 mg of $Ni(ClO_4)_2.6H_2O$ in Example 1, whereby a metal-containing indoaniline compound having the formula was obtained.

The melting point of this compound was over 300° C., and the visible range absorption spectrum (in a solvent mixture of chloroform and N,N-dimethylformamide) was $\lambda_{max}$ 794 nm. The results of the elemental analysis were as follows, where the analytical values and the calculated values are in good agreement.

|  | C | H | N |
|---|---|---|---|
| Calculated values (%) | 53.31 | 4.70 | 9.32 |
| Analytical values (%) | 53.43 | 4.69 | 9.40 |

(b) Recording medium

In the same manner as in Example 1, the metal-containing indoaniline compound prepared in step (a) was coated by a spinner method onto a PMMA resin substrate (52 mm in diameter).

The maximum absorption wavelength of the coating layer was 800 nm, and the shape of the spectrum was broad.

(c) Optical recording

To the above coating layer, a semiconductor laser beam having a central wavelength of 830 nm was irradiated at an output of 6 mW, whereupon pits having a clear profile were formed.

The storage stability of this coating layer (60° C., 80% RH) was good.

EXAMPLE 4

(a) Preparation

The operation was conducted in the same manner as in Example 1 except that 86.8 mg of a compound having the formula:

was used instead of 100 mg of the compound having the formula:

and 289 mg of Cu(ClO$_4$)$_2$.6H$_2$O was used instead of 285.3 mg of Ni(ClO$_4$)$_2$.6H$_2$O in Example 1, whereby a metal-containing indoaniline compound having the formula:

was obtained.

Figure 4:
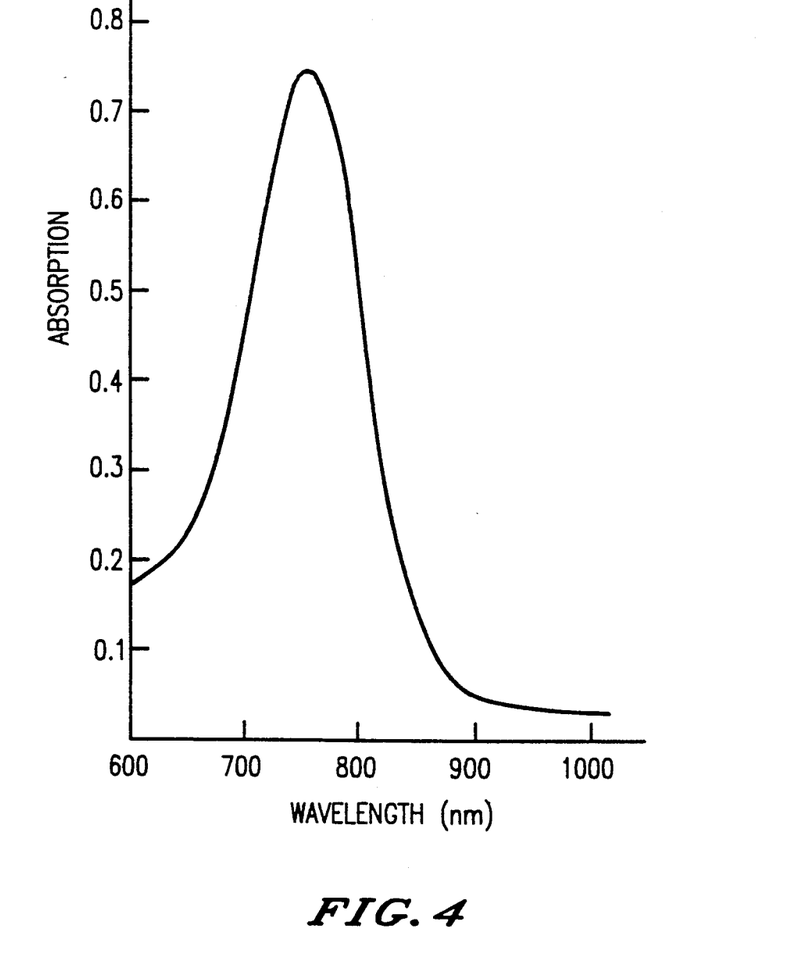

The melting point of this compound was over 300° C., and the visible range absorption spectrum (in a solvent mixture of chloroform and N,N-dimethylformamide) was $\lambda_{max}$ 760 nm (FIG. 4). The results of the elemental analysis are shown below, where the analytical values and the calculated values are in good agreement.

|  | C | H | N |
|---|---|---|---|
| Calculated values (%) | 49.98 | 3.70 | 10.29 |
| Analytical values (%) | 49.65 | 3.62 | 10.25 |

(b) Recording medium

In the same manner as in Example 1, the metal-containing indoaniline compound prepared in step (a) was coated by a spinner method onto a PMMA resin substrate (52 mm in diameter).

The maximum absorption wavelength of the coating layer was 780 nm, and the shape of the spectrum was broad.

(c) Optical recording

To the above coating layer, a semiconductor laser beam having a central wavelength of 780 nm was irradiated, whereupon pits having a clear profile were formed.

The storage stability of this coating layer 60° C., 80% RH) was good.

EXAMPLE 5

In the same manner as in Example 1, metal-containing indoaniline compounds represented by the formula in Table 1 were prepared. The maximum absorption wavelength ($\lambda_{max}$, nm) in a chloroform solution was shown in Table 1.

TABLE 1

| No. | Structural formula | Maximum absorption wavelength in the solution (nm) |
|---|---|---|
| 5-1 | Ni²⁺ complex with N,N-di-n-propyl, CH₃ substituent, (ClO₄⁻)₂ | 796 |
| 5-2 | Ni²⁺ complex with N-ethyl-N-n-propyl, CH₃ substituent, (ClO₄⁻)₂ | 796 |
| 5-3 | Ni²⁺ complex with N,N-di-n-butyl, CH₃ substituent, (ClO₄⁻)₂ | 800 |
| 5-4 | Ni²⁺ complex with N-ethyl-N-n-butyl, CH₃ substituent, (ClO₄⁻)₂ | 798 |
| 5-5 | Ni²⁺ complex with N,N-di-n-pentyl, CH₃ substituent, (ClO₄⁻)₂ | 800 |
| 5-6 | Ni²⁺ complex with N,N-di-n-hexyl, CH₃ substituent, (ClO₄⁻)₂ | 802 |
| 5-7 | Ni²⁺ complex with N,N-di-n-propyl, (ClO₄⁻)₂ | 774 |

TABLE 1-continued

| No. | Structural formula | Maximum absorption wavelength in the solution (nm) |
|---|---|---|
| 5-8 | [Ni²⁺ complex with O, N ligand, =N–C₆H₄–N(C₄H₉(n))₂]₂ (ClO₄⁻)₂ | 776 |
| 5-9 | [Ni²⁺ complex with O, N ligand, =N–C₆H₄–N(C₅H₁₁(n))₂]₂ (ClO₄⁻)₂ | 776 |
| 5-10 | [Ni²⁺ complex with O, N ligand, =N–C₆H₄–N(C₆H₁₃(n))₂]₂ (ClO₄⁻)₂ | 778 |
| 5-11 | [Ni²⁺ complex with O, N ligand, =N–C₆H₃(CH₃)–N(C₄H₉(n))₂, with CH₃ substituent]₂ (ClO₄⁻)₂ | 802 |
| 5-12 | [Ni²⁺ complex with O, N ligand, =N–C₆H₄–N(C₃H₇(n))₂, with CH₃ substituent]₂ (ClO₄⁻)₂ | 774 |
| 5-13 | [Ni²⁺ complex with O, N ligand, Cl substituent, =N–C₆H₃(CH₃)–N(C₂H₅)₂]₂ (ClO₄⁻)₂ | 802 |

TABLE 1-continued

| No. | Structural formula | Maximum absorption wavelength in the solution (nm) |
|---|---|---|
| 5-14 |  | 795 |
| 5-15 |  | 796 |
| 5-16 |  | 795 |
| 5-17 |  | 797 |
| 5-18 |  | 774 |
| 5-19 |  | 796 |
| 5-20 |  | 797 |

TABLE 1-continued

| No. | Structural formula | Maximum absorption wavelength in the solution (nm) |
|---|---|---|
| 5-21 | [Co²⁺ complex with quinone-imine ligand, N(C₂H₅)₂, CH₃] (ClO₄⁻)₂ | 792 |
| 5-22 | [Co²⁺ complex with quinone-imine ligand, N(C₄H₉(n))₂, CH₃] (Cl⁻)₂ | 794 |
| 5-23 | [Cu²⁺ complex with Cl-substituted quinone-imine ligand, N(C₄H₉(n))₂, CH₃, CH₃] (Br⁻)₂ | 803 |
| 5-24 | [Co²⁺ complex with quinone-imine ligand, N(C₃H₇(n))₂, CH₃, CH₃] (ClO₄⁻)₂ | 800 |
| 5-25 | [Ni²⁺ complex with quinone-imine ligand, N(C₃H₇(n))₂, C₂H₅] (ClO₄⁻)₂ | 801 |
| 5-26 | [Ni²⁺ complex with quinone-imine ligand, N(C₃H₇(n))₂, C₂H₅] (Cl⁻)₂ | 801 |

TABLE 1-continued

| No. | Structural formula | Maximum absorption wavelength in the solution (nm) |
|---|---|---|
| 5-27 |  | 801 |
| 5-28 |  | 800 |
| 5-29 |  | 803 |
| 5-30 |  | 801 |
| 5-31 |  | 808 |
| 5-32 |  | 806 |

TABLE 1-continued

| No. | Structural formula | Maximum absorption wavelength in the solution (nm) |
| --- | --- | --- |
| 5-33 |  | 790 |

What is claimed is:

1. An optical recording medium comprising a substrate and a recording layer containing a dye formed on the substrate wherein the recording is effected by irradiation of a laser beam to occur a thermal deformation of the recording layer and the reproduction is done by reading a difference in the reflectance between the deformed portion and the undeformed portion, said dye being a metal-containing indoaniline compound having the formula:

wherein M is a metal atom selected from the group consisting of Ni, Cu or Co, $R^1$ is a hydrogen atom, a halogen atom or a methyl group, n is 1 or 2, X is a hydrogen atom or a lower alkyl group each of $R^2$ and $R^3$ is a lower alkyl group, and $Z^-$ is an anion.

2. The optical recording medium according to claim 1, wherein M in the formula I is Ni.

3. The optical recording medium according to claim 1, wherein X in the formula I is an alkyl group having 1 or 2 carbon atoms.

4. The optical recording medium according to claim 1, wherein X in the formula I is an ethyl group.

5. The optical recording medium according to claim 1, wherein each of $R^2$ and $R^3$ in the formula I is an alkyl group having from 2 to 4 carbon atoms.

6. The optical recording medium according to claim 1, wherein $Z^-$ in the formula I is an anion selected from the group consisting of $Br^-$, $Cl^{-Z}$, $I^-$ and $ClO_4^-$.

7. The optical recording medium according to claim 1, wherein $R^1$ in the formula, I is a hydrogen atom.

8. The optical recording medium according to claim 1, wherein the metal-containing indoaniline compound has the formula:

wherein each of $R^4$ and $R^5$ is an alkyl group having from 2 to 4 carbon atoms.

9. The optical recording medium according to claim 1, wherein the substrate is made of a material selected from the group consisting of a methacrylate resin and a polycarbonate resin.

10. The optical recording medium according to claim 1, wherein the recording layer has a thickness of from 100 Å to 5 μm.

* * * * *